United States Patent [19]
Kauffman et al.

[11] Patent Number: 6,100,035
[45] Date of Patent: Aug. 8, 2000

[54] METHOD OF IDENTIFYING CIS ACTING NUCLEIC ACID ELEMENTS

[75] Inventors: Stuart A. Kauffman, Santa Fe, N. Mex.; Marc Ballivet, Geneva, Switzerland

[73] Assignee: Cistem Molecular Corporation, San Diego, Calif.

[21] Appl. No.: 09/165,794

[22] Filed: Oct. 2, 1998

Related U.S. Application Data
[60] Provisional application No. 60/092,697, Jul. 14, 1998.

[51] Int. Cl.$^7$ ...................................................... C12Q 1/68
[52] U.S. Cl. .................................................................. 435/6
[58] Field of Search ..................................................... 435/6

[56] References Cited

U.S. PATENT DOCUMENTS

| | | |
|---|---|---|
| 5,270,163 | 12/1993 | Gold et al. . |
| 5,306,619 | 4/1994 | Edwards et al. . |
| 5,567,588 | 10/1996 | Gold et al. . |
| 5,578,444 | 11/1996 | Edwards et al. . |
| 5,582,981 | 12/1996 | Toole et al. . |
| 5,595,877 | 1/1997 | Gold et al. . |
| 5,637,459 | 6/1997 | Burke et al. . |
| 5,670,637 | 9/1997 | Gold et al. . |
| 5,683,867 | 11/1997 | Biesecker et al. . |
| 5,688,935 | 11/1997 | Stephens et al. . |
| 5,693,463 | 12/1997 | Edwards et al. . |
| 5,696,249 | 12/1997 | Gold et al. . |
| 5,705,337 | 1/1998 | Gold et al. . |
| 5,712,375 | 1/1998 | Jensen et al. . |
| 5,723,289 | 3/1998 | Eaton et al. . |
| 5,723,592 | 3/1998 | Eaton et al. . |
| 5,726,014 | 3/1998 | Edwards et al. . |
| 5,750,342 | 5/1998 | Stephens et al. . |
| 5,763,177 | 6/1998 | Gold et al. . |
| 5,763,566 | 6/1998 | Jensen et al. . |
| 5,763,595 | 6/1998 | Gold et al. . |
| 5,773,598 | 6/1998 | Burke et al. . |
| 5,789,157 | 8/1998 | Jensen et al. . |
| 5,789,160 | 8/1998 | Eaton et al. . |
| 5,817,785 | 10/1998 | Gold et al. . |
| 5,843,653 | 12/1998 | Gold et al. . |
| 5,853,984 | 12/1998 | Davis et al. . |
| 5,858,660 | 1/1999 | Eaton et al. . |
| 5,861,246 | 1/1999 | Weisman et al. ............................ 435/6 |
| 5,861,254 | 1/1999 | Schneider et al. . |
| 5,864,026 | 1/1999 | Jensen et al. . |
| 5,874,218 | 2/1999 | Drolet et al. . |

FOREIGN PATENT DOCUMENTS

| | | |
|---|---|---|
| 0347915A | 12/1989 | European Pat. Off. . |
| WO 89/06694 | 7/1989 | WIPO . |
| WO 95/05389A | 8/1993 | WIPO . |
| WO 94/24314 | 10/1994 | WIPO . |
| WO 97/27330 | 7/1997 | WIPO . |

OTHER PUBLICATIONS

Grossman et al., "The use of antibodies to the polypyrimidine tract binding protein (PTB) to analyze the protein components that assemble on alternatively spliced pre-m-RNAs that use distant branch points," *RNA* 4:613–625 (1998).

Yu et al., "Specific binding of host cellular proteins to multiple sites within the 3' end of mouse hepatitis virus genomic RNA," *Journal of Virology* 69:2016–2023 (1995).

Blackwell, "Selection of Protein Binding Sites from Random Nucleic Acid Sequences," *Methods in Enzymology* 254:604–618 (1995).

Ellington and Szostak, "In vitro selection of RNA molecules that bind specific ligands," *Nature* 346:818–822 (1990).

Funk and Wright, "Cyclic amplification and selection of targets for multicomponent complexes: Myogenin interacts with factors recognizing binding sites for basic helix–loop–helix, nuclear factor 1, myocyte–specific enhancer binding factor 2, and COMP1 factor," *Proc. Natl. Acad. Sci. USA* 89:9484–9488 (1992).

Hagenbuchle and Wellauer, "A rapid method for the isolation of DNA–binding proteins from purified nuclei of tissues and cells in culture," *Nucleic Acids Research* 20:3555–3559 (1992).

Mavrothalassitis et al., "Defining Target Sequences of DNA–Binding Proteins by Random Selection and PCR: Determination of the GCN4 Binding Sequence Repertoire," *DNA and Cell Biology* 9:783–788 (1990).

Nallur et al., "Multiplex selection technique (MuST): An approach to clone transcription factor binding sites," *Proc. Natl. Acad. Sci. USA* 93:1184–1189 (1996).

Nørby et al., "Determination of recognition–sequences for DNA–binding proteins by a pollymerase chain reaction assisted binding site selection method (BSS) using nitrocellulose immobilized DNA binding protein," *Nucleic Acids Research* 20:6317–6321 (1992).

Pollock and Treisman, "A sensitive method for the determination of protein–DNA binding specificities," *Nucleic Acids Research* 18:6197–6204 (1990).

Wright and Funk, "CASTing for multicomponent DNA–binding complexes," *TIBS* 18:77–80 (1993).

Wright et al., "Cyclic Amplification and Selection of Target (CASTing) for the Myogenin Consensus Binding Site," *Molecular and Cellular Biology* 11:4104–4110 (1991).

(List continued on next page.)

*Primary Examiner*—Terry McKelvey

[57] ABSTRACT

The invention provides a method of identifying nucleic acid molecules that contain cis acting nucleic acid elements. Also provided is a method of isolating nucleic acid binding factors. The invention also provides methods of identifying compounds that are cis acting nucleic acid element analogs, compounds that are nucleic acid binding factor analogs, compounds that selectively bind cis acting nucleic acid elements and compounds that selectively displace binding between a nucleic acid binding factor and a cis acting nucleic acid element or between nucleic acid binding factors. Also provided is a method of determining a binding state of a nucleic acid. Pluralities of isolated nucleic acid molecules containing cis acting nucleic acid elements, of isolated cis acting nucleic acid elements and of isolated nucleic acid binding factors are also provided. The invention further provides methods of treating pathological conditions using molecules of the invention to alter genetic activities of nucleic acids involved in pathological conditions.

11 Claims, No Drawings

OTHER PUBLICATIONS

Düzgünes and Felgner, "Intracellular Delivery of Nucleic Acids and Transcription Factors by Cationic Liposomes," *Methods In Enzymology*, 221:303–306 (1993).

Fitzwater and Polisky, A SELEX Primer, "A SELEX Primer," *Nucleic Acid Libraries*, Chapter 17, pp. 275–301 (1996).

Gold et al., "Diversity of Oligonucleotide Functions," *Annu. Rev. Biochem.*, 64:763–797 (1995).

Gold et al., "From Oligonucleotide Shapes to Genomic SELEX: Novel Biological Regulatory Loops," *Proc. Natl. Acad. Sci. USA*, 94:59–64 (1997).

Gold et al., "SELEX and the Evolution of Genomes," *Current Opinion in Genetics & Development*, 7:848–851 (1997).

Hardenbol et al., "Identification of Preferred hTBP DNA Binding Sites by the Combinatorial Method REPSA," *Nucleic Acids Research*, 25:3339–3344 (1997).

Isalan et al., "Comprehensive DNA Recognition through Concerted Interactions from Adjacent Zinc Fingers," *Biochemistry*, 37:12026–12033 (1988).

Kinzler and Bogelstein, "Whole Genome PCR: application to the identification of sequences bound by gene regulatory proteins," *Nucleic Acids Research*, 17(10):3645–3653 (1989).

Morishita et al., "Application of Transcription Factory "Decoy" Strategy as Means of Gene Therapy and Study of Gene Expression in Cardiovascular Disease," *Cir Res*, 82:1023–1028 (1998).

Morris et al., "High affinity ligands from in vitro selection: Complex targets," *Proc. Natl. Acad. Sci. USA*, 95:2902–2907 (1988).

Nallur et al., "Multiplex Selection Technique (MuST): An Approach to Clone Transcription Factor Binding Sites," *Proc. Natl. Acad. Sci. USA*, 93:1184–1189 (1996).

Oliphant et al., "Cloning of random–sequence oligodeoxynucleotides," *Gene*, 44:177–183 (1986).

Oliphant et al., "Defining the Sequence Specificity of DNA–Binding Proteins by Selecting Sites from Random–Sequence Oligonucleotides: Analysis of Yeast GCN4 Protein," *Mol. and Cell. Biol.*, 9(7):2944–2949 (1989).

Oliphant, A. et al., "The Use of Random–Sequence Oligonucleotides for Determining Consensus Sequences," *Methods in Enzymology*, 155:568–582 (1987).

Rebar and Pabo, "Zinc Finger Phage: Affinity Selection of Fingers with New DNA–Binding Specificities," *Science*, 263:671–673 (1994).

Singer et al., "Libraries for genomic SELEX," *Nucleic Acids Research*, 25(4):781–786 (1997).

Sullenger et al., "Analysis of trans–Acting Response Decoy RNA–Mediated Inhibition of Human Immunodeficiency Virus Type 1 Transactivation," *J. of Virology*, 65(12):6811–6816 (1991).

Thiesen and Bach, "Target Detection Assay (TDA): a versatile procedure to determine DNA binding sites as demonstrated on SP1 protein," *Nucleic Acids Research*, 18(11):3203–3209 (1990).

Tuerk, Craig, "Using the SELEX Combinatorial Chemistry Process to Find High Affinity Nucleic Acid Ligands to Target Molecules," 67:219–230 (19!!).

Vant–Hull et al., "The Mathematics of SELEX Against Complex Targets," *J. Mol. Biol.*, 278:579–597 (1998).

METHOD OF IDENTIFYING CIS ACTING NUCLEIC ACID ELEMENTS

This application is based on, and claims the benefit of, U.S. Provisional Application Ser. No. 60/092,697, filed Jul. 14, 1998. The contents of such related application are incorporated herein by reference in their entirety.

BACKGROUND OF THE INVENTION

This invention relates to the identification and use of cis acting nucleic acid elements that bind to nucleic acid binding factors to regulate genetic activities of nucleic acids.

All living creatures store information in nucleic acid molecules called DNA or RNA that encode structural and regulatory proteins. The collective behavior of nucleic acids and proteins constitutes and controls normal cell and organismal life cycles. Nucleic acids and proteins also act as causative agents in, or response factors to, pathological conditions.

Transcription of DNA into RNA, translation of RNA into proteins and other genetic events such as nucleic acid synthesis, sorting, processing, repair and degradation, are regulated by a variety of specialized nucleic acid binding factors. Nucleic acid binding factors bind to specific sequences present on the nucleic acid molecules they regulate, called cis acting nucleic acid elements. These nucleic acid binding factors, bound to their specific cis acting nucleic acid elements, are able to interact with other cellular factors to modulate specific genetic events. The binding of a nucleic acid binding factor to a cis acting nucleic acid element, or its ability to interact with other factors that mediate genetic events, or both, can be regulated in response to signals transmitted into the cell from the cell exterior.

As an example, regulatory proteins called "transcription factors" bind to cis acting nucleic acid elements on genomic DNA at sites known as "promoters" and "enhancers" present at variable distances from the site of initiation of transcription of the genes they regulate. The enhancer sequences and adjacent nucleic acid sequences, together with their bound transcription factors, are able to bend to contact the transcriptional complex bound to the promoter. Such contact can either enhance or reduce expression of the regulated gene.

The human genome, which stores the genetic information of a human cell as DNA, is estimated to contain about 100,000 genes. Each of these genes and the RNAs they encode is likely to have multiple cis acting nucleic acid elements that bind to corresponding nucleic acid binding factors to regulate gene expression. These cis acting nucleic acid elements, and the factors that bind them, are potential targets for therapeutic drugs that could be used to modulate gene expression. Determining which cis acting nucleic acid elements are bound under different conditions can also be used to characterize and monitor the genetic responses of a cell under normal, pathological or experimental conditions.

Current methods of identifying cis acting nucleic acid elements have several disadvantages. Most of these methods require prior identification of either the nucleic acid that is regulated, or the corresponding regulatory nucleic acid binding factor, or both. For example, once a nucleic acid has been identified, adjacent sequences, which are predicted to contain cis acting nucleic acid elements, can be isolated and subsequences therefrom are tested for cis activities. Alternatively, once a nucleic acid binding factor has been isolated, the sequences to which it binds can be identified. Other methods, which are limited to identifying transcriptional enhancer elements, involve cloning random nucleic acid sequences upstream of a reporter gene and observing expression of the reporter gene product.

At present, however, there is no broadly applicable method to identify cis acting nucleic acid elements without prior identification of the regulated nucleic acid or of the regulatory nucleic acid binding factor. There is also no rapid and efficient method to simultaneously identify a plurality of cis acting nucleic acid elements.

Thus, there exists a need for a method of rapidly and efficiently identifying cis acting nucleic acid elements. The present invention satisfies this need and provides related advantages as well.

SUMMARY OF THE INVENTION

The invention provides a method of identifying nucleic acids containing cis acting nucleic acid elements. The method consists of contacting a diverse population of nucleic acid binding factors with a diverse population of isolated nucleic acid molecules under conditions that allow the nucleic acid binding factors to selectively bind the nucleic acids. The nucleic acids that bind the nucleic acid binding factors are identified and are characterized as nucleic acids containing cis acting nucleic acid elements. The method simultaneously provides for the isolation of nucleic acid binding factors that selectively bind the isolated nucleic acid molecules.

The invention also provides methods of identifying compounds that are cis acting nucleic acid element analogs, compounds that are nucleic acid binding factor analogs, and compounds that selectively bind cis acting nucleic acid elements. The invention further provides methods to identify compounds that selectively displace binding between a nucleic acid binding factor and a cis acting nucleic acid element or between nucleic acid binding factors.

The invention further provides a plurality of isolated nucleic acid molecules that each contain one or more cis acting nucleic acid elements. Also provided is a plurality of isolated cis acting nucleic acid element analogs. The isolated nucleic acid molecules containing cis acting nucleic acid elements and the isolated cis acting nucleic acid element analogs in the pluralities can be bound to nucleic acid binding factors. A plurality of isolated nucleic acid binding factors is also provided.

The invention also provides a method of determining a binding state of a nucleic acid. The method consists of contacting a nucleic acid with a plurality of isolated cis acting nucleic acid elements under conditions that allow nucleic acid binding factors bound to the nucleic acid to bind to the isolated cis acting nucleic acid elements. The isolated cis acting nucleic acid elements that bind the nucleic acid binding factors are identified and characterize the binding state of the nucleic acid.

The invention further provides a method of treating a pathological condition in an individual. The method consists of administering to the individual an effective amount of a therapeutic agent that selectively alters the ability of a cis acting nucleic acid element to regulate a genetic activity of a nucleic acid involved in the pathological condition. Also provided is a method of treating a pathological condition in an individual by contacting a cell of the individual with an effective amount of a targeting construct that includes a cis acting nucleic acid element and targeting sequences. The targeting construct is taken up by the cell and inserted by homologous recombination into a nucleic acid involved in the pathological condition so as to alter a genetic activity of the nucleic acid.

DETAILED DESCRIPTION OF THE INVENTION

The present invention is directed to the identification and use of cis acting nucleic acid elements.

Cis acting nucleic acid elements and the binding factors that selectively bind such elements regulate the genetic circuitry that controls all aspects of cell and organismal growth and development. Cis acting nucleic acid elements regulate genetic activities that underlie growth and development, including, for example, replication of nucleic acids and expression of both nucleic acids and proteins. Therefore, cis acting nucleic acid elements and their corresponding nucleic acid binding factors are targets for therapeutic agents that modulate cell or tissue growth, development, pathogenesis, regeneration or repair by altering, enhancing or reducing the genetic activity of the nucleic acids they regulate.

Compounds that selectively bind cis acting nucleic acid elements, that selectively bind nucleic acid binding factors, or that selectively displace binding of a cis acting nucleic acid element to its binding factor, are all potential therapeutic agents that can modulate a genetic activity of a nucleic acid regulated by the cis acting nucleic acid element. Furthermore, isolated cis acting nucleic acid elements and the corresponding nucleic acid binding factors can themselves be used as therapeutic agents to selectively modulate a genetic activity. Cis acting nucleic acid elements can also be used to identify and isolate a nucleic acid or group of nucleic acids that are modulated by the cis acting nucleic acid elements, such as a gene or a family of genes involved in a particular disease or that regulate a particular stage of development.

In one embodiment, the invention provides methods of identifying cis acting nucleic acid elements. The methods are advantageous in allowing rapid and efficient identification of cis acting nucleic acid elements without prior knowledge of the nucleic acid sequences they regulate or of the corresponding nucleic acid binding factors that bind the cis acting elements. The methods provide a means of simultaneously identifying cis acting nucleic acid elements that modulate a genetic activity of a plurality of nucleic acids. Cis acting nucleic acid elements can be used as therapeutic agents or to screen for therapeutic agents, as well as to diagnose disease.

In another embodiment, the invention provides methods for identifying nucleic acid binding factors that bind to cis acting nucleic acid elements without prior knowledge of either the cis acting nucleic acid elements they bind or the nucleic acid sequences they regulate. The methods are advantageous in providing a means of simultaneously identifying nucleic acid binding factors that modulate a genetic activity of a plurality of nucleic acids. Nucleic acid binding factors can be used as therapeutic agents or to screen for therapeutic agents that selectively target a nucleic acid or group of nucleic acids.

In yet another embodiment, the invention provides methods of identifying compounds that are analogs of cis acting nucleic acid elements or of nucleic acid binding factors, or that displace binding of cis acting nucleic acid elements to nucleic acid binding factors. The methods are advantageous in that they provide a rapid and efficient means of screening for compounds that can be used as therapeutic agents to modulate a genetic activity of a nucleic acid or group of nucleic acids involved in disease.

In another embodiment, the invention is directed to a method of determining the binding state of one or a plurality of nucleic acids. The binding of a nucleic acid binding factor to a cis acting nucleic acid element is generally required for its regulatory activity. Therefore, the binding state of a nucleic acid or a plurality of nucleic acids is a means of characterizing the activation state of the nucleic acid or plurality of nucleic acids. Such a characterization can be used for a variety of purposes such as, for example, diagnosing pathological conditions or monitoring the efficacy of therapeutic procedures.

As used herein, the term "cis acting nucleic acid element" refers to a single-stranded or double-stranded RNA or DNA sequence that can be selectively bound by nucleic acid binding factors to regulate one or more genetic activities of a nucleic acid sequence present on the same molecule. Cis acting nucleic acid elements are present in all organisms, including prokaryotes, eukaryotes and viruses. For example, cis acting nucleic acid elements are present in yeast, animals, plants, bacteria and viruses.

Cis acting DNA elements are found in a variety of different types of DNA including, for example, genomic, mitochondrial and chloroplast DNA. Cis acting DNA elements are also located at a variety of locations on chromosomes. For example, cis acting DNA elements are located at diverse locations within chromosomes, such as within transcription units or at the domain boundaries of transcriptional units, as well as at the centromeres, kinetochores and telomeres of chromosomes. Cis acting DNA elements can regulate a variety of genetic activities including, for example, enhancing, attenuating or repressing transcription of a structural or regulatory gene or operon. A cis acting DNA element can also regulate, for example, replication, repair, packaging, modification, restriction or degradation of a DNA sequence.

Cis acting DNA elements also include nucleic acid elements that modulate the assembly or structural integrity of DNA. A specific example of a cis acting DNA element that modulates the assembly or structural integrity of DNA is a boundary element that selectively binds to scaffold proteins and serves to define transcriptional domains of chromatin. Additionally, cis acting DNA elements are present at kinetochores, centromeres or telomeres of chromosomes and modulate the assembly and structural integrity of DNA.

Cis acting RNA elements are also found in a variety of different types of RNAs including, for example, messenger RNA (mRNA), ribosomal RNA (rRNA), transfer RNA (tRNA), heterogeneous nuclear RNA (hnRNA), small nuclear or small cytoplasmic RNA (snRNA or scRNA) and viral RNA. Cis acting RNA elements can regulate a variety of genetic activities including, for example, RNA translation, replication, splicing, editing, intracellular transport, localization, degradation and reverse transcription.

The types of cis acting nucleic acid elements present in nucleic acids vary depending on the cell and nucleic acid type. For example, transcription of eukaryotic DNA involves a variety of cis acting nucleic acid elements such as promoter elements, enhancer elements and response elements. Certain of these cis acting nucleic acid elements, for example, TATA boxes, are found in a majority of genes. Other cis acting nucleic acid elements, for example, hormone response elements, are characteristic of genes that are coordinately regulated. Some cis acting nucleic acid elements bind to nucleic acid binding factors in a tissue-specific or temporal manner, whereas others are constitutively bound by nucleic acid binding factors. Although individual cis acting nucleic acid elements can be involved in the regulation of many different nucleic acids, a particular combination of cis acting nucleic acid elements can be specific for one or only a limited number nucleic acids.

A cis acting nucleic acid element can be localized within the nucleic acid sequence it regulates, or upstream or downstream thereof. A cis acting nucleic acid element can be a contiguous nucleic acid sequence, or a multi-partite sequence. For example, a nucleic acid binding factor or complex of factors can bind to a continuous cis acting nucleic acid element or to two or more discontinuous nucleic acid sequences that are in close proximity due to folding or looping of the polynucleotide, that together form a nucleic acid element. A cis acting nucleic acid element is generally from about 4 to about 100 nucleotides in length, and is more typically from about 6 to about 25 nucleotides in length.

The methods of the invention are applicable to the identification and use of cis acting nucleic acid elements of a wide variety of nucleic acid types and sizes, and from any organism. The methods of the invention also allow the identification and use of cis acting nucleic acid elements or combinations of cis acting nucleic acid elements that modulate any regulatory or structural genetic activity, and that modulate any subset of nucleic acids that is of interest.

As used herein, the term "selective binding" or "selectively binds," when used in connection with binding between a cis acting nucleic acid element and either a nucleic acid binding factor or a compound, refers to binding with substantially higher affinity to a nucleic acid having a sequence that is substantially similar to the sequence of a particular cis acting nucleic acid element than to a nucleic acid that lacks substantial similarity to the sequence of a particular cis acting nucleic acid element. The degree or extent of nucleic acid sequence similarity required for selective binding of a nucleic acid binding factor or compound to a particular cis acting nucleic acid element depends on, for example, the length and sequence composition of the cis acting nucleic acid element and the nature of the binding interaction. Such selective binding can be determined either qualitatively or quantitatively by known methods, such as by competition with nucleic acids of similar or different sequences to the cis acting nucleic acid element.

Selective binding between a nucleic acid binding factor and a compound refers to binding with substantially higher affinity to a substantially similar binding factor or compound than to an unrelated binding factor or compound. Selective binding between a nucleic acid binding factor and a compound can similarly be determined by, for example, competition for, or displacement of, binding with substantially similar binding factors and compounds, as compared with binding factors and compounds that lack substantially similarity. Selective binding between a nucleic acid binding factor and a compound that is a cis acting nucleic acid element analog can further be determined by an ability of a nucleic acid containing a sequence that is substantially similar to a cis acting nucleic acid element to compete for binding with the analog compound for the binding factor, such that the analog compound is selectively displaced.

As used herein, the term "diverse population of isolated nucleic acid molecules" refers to a composition comprising a plurality of different isolated polynucleotide nucleic acid molecules that potentially contain cis acting nucleic acid elements. The diverse population of nucleic acids used in the methods of the invention can be of a variety of different types, structures and topology. The choice of nucleic acid type, structure and topology will depend on the need and desired result. For example, the diverse populations of nucleic acids of the invention can include double-stranded or single-stranded DNA or RNA, as well as linear, circular or branched nucleic acid molecules.

The term "isolated," when used in reference to isolated nucleic acid molecules, is intended to mean that the nucleic acid molecules are present in a form or state different from how they are found in nature. Similarly, the term "isolated," when used in reference to isolated nucleic acid binding factors, is intended to mean that the nucleic acid binding factors are present in a form or state different from how they are found in nature. For example, the isolated molecules can be different than populations found in nature in that they are substantially purified and therefore are free of molecules other than nucleic acids or other than nucleic acid binding factors. Such molecules can also be different than molecules found in nature in that they are, for example, produced or expressed by recombinant means or synthesized by chemical means. Such recombinantly or chemically produced molecules therefore do not contain some or many of the normal cellular components as they are found in nature or as they are isolated from natural sources and can also differ in multiplicity or homogeneity from populations of molecules found in nature. Furthermore, such molecules can also be different than molecules found in nature in that they are bound or immobilized, with or without cellular constituents, on a filter or solid support. Isolated molecules can also be different from the state or form found in nature in that they are detectably labeled or contain non-native nucleic acid sequences.

A population of different isolated nucleic acid molecules can be prepared, or obtained, that is of any diversity that is appropriate for a particular application of a method of the invention. A population of nucleic acids of low diversity can contain, for example, 2, 3, 4, 5, 6, 7, 8, 9, between about 10 and 20, between about 21 and 80, or between about 81 and 200 different nucleic acid molecules. For certain applications of the method, it may be preferable to begin with a population of nucleic acids of moderate diversity, containing, for example, between about 200 and $10^3$, preferably greater than about $10^4$, more preferably greater than about $10^5$ different nucleic acid molecules. If desired, using currently available methods, it is possible to synthesize a population of isolated nucleic acid molecules of high diversity, containing, for example, between about $10^6$ and $10^8$ different nucleic acid molecules, preferably between about $10^9$ and $10^{11}$ different nucleic acid molecules, most preferably about $10^{13}$ different nucleic acid molecules. As an example, a population that includes all possible molecules of between 5 and 20 nucleotides in length, including each of the four naturally occurring nucleotides at each position, would have approximately $4^5+4^6+4^7+\ldots 4^{20}$ or approximately $10^{13}$ different nucleic acid molecules. Such a population of about $10^{13}$ 20 different nucleic acid molecules inherently includes all possible cis acting nucleic acid elements of up to about 20 nucleotides in length.

A diverse population of isolated nucleic acid molecules can be of completely random composition or of partially or completely known composition, so long as some nucleic acid sequences within the population are different. One skilled in the art would be able to determine the extent of diversity and degree of randomness required for a particular application of the method.

A diverse population of isolated nucleic acid molecules includes nucleic acid molecules potentially containing cis acting nucleic acid elements. Depending on the application of the method, a diverse population of isolated nucleic acid molecules can include single-stranded or double-stranded RNA or DNA molecules, or any combination thereof. The isolated nucleic acid molecules in the diverse population can be from about 4 to about 1000 nucleotides in length and can include molecules of the same or of varying lengths. If desired, some or all of the isolated nucleic acid molecules can include, or be flanked at one or both ends by, known sequences, such as sequences homologous to oligonucleotide primers for the polymerase chain reaction (PCR), sequences containing restriction sites, or detectable sequences.

As used herein, the term "nucleic acid binding factor" is a factor that selectively binds a cis acting nucleic acid element to modulate a genetic activity of a nucleic acid or group of nucleic acids. Modulation can include, for example, enhancing, repressing or attenuating the regulation of a nucleic acid. Nucleic acid binding factors include, for example, transcription factors, replication factors, translation factors, restriction and modifying factors, structural and assembly factors, and other molecules involved in regulating one or more genetic activities of a nucleic acid sequence. Nucleic acid binding factors also include factors involved in the structural integrity of chromatin or chromosomes, such as, for example, scaffold proteins and other factors that selectively bind to boundary elements, kinetochores, centromeres and telomeres.

A nucleic acid binding factor can interact covalently or non-covalently with other factors to form a complex that binds a cis acting nucleic acid element. The factors within such a binding complex are also included within the term "nucleic acid binding factor." Some nucleic acid binding factors within a complex of nucleic acid binding factors can contact a cis acting nucleic acid element directly. Other nucleic acid binding factors within a complex of nucleic acid binding factors do not contact a cis acting nucleic acid element directly, but can contact one or more other nucleic acid binding factors. Disrupting the interaction between two or more nucleic acid binding factors within a complex, or between nucleic acid binding factors and a cis acting nucleic acid element, will alter the ability of the cis acting nucleic acid element to modulate a genetic activity of the nucleic acid it regulates.

A nucleic acid binding factor can be a polypeptide or a polypeptide that is modified, for example, by phosphorylation or addition of one or more carbohydrates, nucleotides, nucleic acids, cofactors or lipids. A nucleic acid binding factor can also be a non-proteinaceous molecule, such as a lipid, carbohydrate or nucleic acid, or any combination thereof.

As used herein, the term "diverse population of nucleic acid binding factors" is intended to mean a composition containing a plurality of different nucleic acid binding factors. The greater the number of different factors within the population, the greater the diversity of the population. A population of nucleic acid binding factors can be of low diversity for certain applications of the method. For example, a population of nucleic acid binding factors of low diversity can include, for example, 2, 3, 4, 5, 6, 7, 8, 9, between about 10 and 20, between about 21 and 50, or between about 51 and 100 different nucleic acid binding factors. A population of nucleic acid binding factors of higher diversity can include more than about 100, more than about $10^3$, or more than about $10^4$ different nucleic acid binding factors. As with the diverse populations of isolated nucleic acid molecules, the members within a diverse population of nucleic acid binding factors can be known, unknown or partially known so long as some of the factors are different. One skilled in the art would be able to determine the size and extent of diversity in a population of nucleic acid binding factors required to practice a particular embodiment of the invention.

A diverse population of nucleic acid binding factors can be a population of nucleic acid binding factors that is bound to nucleic acids, or unbound. For example, a population of nucleic acid binding factors bound to nucleic acids can be a cellular nucleic acid preparation that contains nucleic acid binding factors.

Such a preparation can be, for example, a chromatin preparation, a hnRNA preparation, an mRNA preparation, or other nucleic acid preparation that includes nucleic acid binding factors, depending on the type and function of cis acting nucleic acid elements and nucleic acid binding factors that are desired to be obtained. A population of unbound nucleic acid binding factors can be, for example, a population of nucleic acid binding factors eluted from a nucleic acid preparation, or a cellular extract or subset thereof.

As used herein, the term "diverse population of compounds" refers to a plurality of different molecules that potentially includes therapeutic compounds that can be used to selectively bind to cis acting nucleic acid elements, to nucleic acid binding factors, or to both. Therefore, a diverse population of compounds can include analogs of cis acting nucleic acid elements, analogs of nucleic acid binding factors, and molecules that selectively displace the binding between a cis acting nucleic acid element and its corresponding binding factor. Such compounds can be naturally occurring macromolecules, such as polypeptides, nucleic acids, carbohydrates or lipids. However, derivatives, analogs and mimetics of these macromolecules, as well as organic compounds, including polymers and small organic compounds, can also selectively bind a cis acting nucleic acid element or a nucleic acid binding factor.

The extent of diversity of a population of compounds required for a particular application of methods of the invention can be determined by those skilled in the art. Generally, the greater the diversity, the larger the likelihood of identifying a compound that binds a cis acting nucleic acid element or a nucleic acid binding factor, or that displaces binding between a cis acting nucleic acid element and a nucleic acid binding factor. A population of compounds of moderate diversity can readily be produced or obtained that contains greater than about $10^5$ different compounds, more preferably greater than about $10^7$ different compounds. A highly diverse population of compounds that contains greater than about $10^9$, preferably greater than about $10^{11}$, more preferably greater than about $10^{13}$ different compounds, can also be used in a method of the invention and can be readily produced or obtained. A less diverse population of compounds can also be advantageous, for example, if the type of compounds that are likely to bind are known or can be predicted based on, for example, information about the sequence or structure of the cis acting nucleic acid element, the nucleic acid binding factor, or the binding interaction between them.

A diverse population of compounds can include, for example, naturally occurring nucleic acids and modified nucleic acids that contain non-naturally occurring nucleoside analogs or linkages. Such modifications can be advantageous, for example, for increasing resistance to chemical or enzymatic degradation. Various modifications that increase the stability of nucleic acids are known in the art and include, for example, phosphotioate linkages. Methods of producing diverse populations of natural and modified nucleic acids are known in the art.

A diverse population of compounds that potentially includes therapeutic agents that target cis acting nucleic acid elements or nucleic acid binding factors can also include libraries of peptides, carbohydrates or synthetic organic molecule. Peptide libraries can include, for example, diverse populations of chemically synthesized peptides and peptidomimetic molecules. Peptide libraries can also include populations of peptides generated by recombinant means, such as phage display or other recombinant methodologies by which a peptide is or can be associated with the nucleic acid which encodes it. Peptide and peptidomimetic libraries of high diversity can be obtained commercially or can be produced by methods known in the art. A diverse population of compounds that potentially includes therapeutic agents that target cis acting nucleic acid elements or nucleic acid binding factors can be a carbohydrate-based combinatorial library, such as an oligosaccharide and glycoconjugate library. Diverse populations of small synthetic molecules, prepared by combinatorial chemistry methods, are also commercially available or can be produced by means known in the art. For example, a diverse population of organic molecules that share one or more common structural features but vary in reactive groups can be routinely produced. Any of these libraries of compounds, if desired, can be synthesized or immobilized onto a solid support or detectably tagged by methods known in the art to provide a means of detection.

As used herein, the term "binding state" refers to the condition or degree of binding of cis acting nucleic acids by nucleic acid binding factors. Modulation, including activation, repression and attenuation of the genetic properties of a nucleic acid by a cis acting nucleic acid element often requires binding of a nucleic acid binding factor to the cis acting nucleic acid element. Therefore, the binding state of a nucleic acid is a reflection or measurement of the type, degree, or extent of regulation of the nucleic acid.

Determination of a "binding state" can be either qualitative or quantitative. For certain applications, it may be sufficient to determine whether one or a plurality of nucleic acids is or is not bound by any nucleic acid binding factor or by a particular nucleic acid binding factor. For other applications, it may be desirable to determine to what degree or extent a nucleic acid is bound by a nucleic acid binding factor. For example, it may be desirable to determine the percentage of nucleic acids that are bound by a nucleic acid binding factor, or to determine the affinity of a binding interaction. For certain determinations of the binding state, it may also be desirable to identify the nucleic acid binding factor that binds the nucleic acid.

Depending on the particular nucleic acids and isolated cis acting nucleic acid elements used in an application of the method, the term "binding state" can refer to, for example, the "transcriptional state," the "replication state," the "translational state" or other genetic properties of a nucleic acid. Furthermore, the term "binding state" can refer to a binding state of a single nucleic acid or group of nucleic acids. The term "binding state" can also refer to the binding state of a cell, group of cells, or tissue. For example, the term "binding state" can characterize the transcriptional activation state of a gene or a family of genes in a cell type of interest.

The invention provides a method of identifying a nucleic acid containing a cis acting nucleic acid element. The method involves contacting a diverse population of nucleic acid binding factors with a diverse population of isolated nucleic acid molecules under conditions that allow nucleic acid binding factors to selectively bind the nucleic acids. The nucleic acids that selectively bind the nucleic acid binding factors are identified and are characterized as nucleic acids containing a cis acting nucleic acid element.

As described previously, cis acting nucleic acid elements selectively bind nucleic acid binding factors and modulate one or more genetic activities of nearby nucleic acids. Any method of altering the interaction between a cis acting nucleic acid element and a nucleic acid binding factor can be used to alter a genetic activity of the regulated nucleic acid. For example, selective binding between a cis acting nucleic acid element and a nucleic acid binding factor can be displaced by a molecule that selectively binds to either the cis acting nucleic acid element or the nucleic acid binding factor. Such a molecule can be, for example, a nucleic acid containing a cis acting nucleic acid element, a nucleic acid binding factor, or other compound. Similarly, selective binding between a compound and a nucleic acid binding factor can be selectively displaced by either a nucleic acid binding factor or a nucleic acid containing a cis acting nucleic acid element. Likewise, selective binding between a compound and a cis acting nucleic acid element can be selectively displaced by either a cis acting nucleic acid element or a nucleic acid binding factor. The molecules that are displaced and the molecules that effect the displacement, or any combination of these molecules, can be identified and isolated by a method of the invention. Therefore, by providing methods of distinguishing between nucleic acids that are bound by nucleic acid binding factors or other compounds, and nucleic acids that are unbound, the methods of the invention can be applied to the identification and isolation of cis acting nucleic acid elements, nucleic acid binding factors and compounds that bind either cis acting nucleic acid elements or nucleic acid binding factors.

The cis acting nucleic acid elements, nucleic acid binding factors and compounds identified by the methods of the invention can be used for therapeutic purposes to alter the activity of one or a plurality of nucleic acids involved, for example, in disease, development, tissue repair or regeneration. The invention can be used with large, diverse populations of isolated nucleic acid molecules or nucleic acid binding factors, or smaller biased populations that contain, for example, nucleic acid sequences or nucleic acid binding factors that are known or predicted to be localized to a particular genomic region, or that are known or predicted to be indicative of a particular normal or pathological condition.

A diverse population of isolated nucleic acid molecules can be produced or obtained by a variety of means known in the art. Both the diversity of the population and the type of nucleic acids will depend on the particular application of the method. Methods of producing a diverse population of isolated nucleic acid molecules are well known, and include, for example, biochemical and recombinant methods as well as by chemical synthesis. For example, a diverse population of isolated nucleic acid molecules can be obtained by cleaving an appropriate cellular or viral source of nucleic acids into smaller fragments by enzymatic, mechanical or chemical means. Fragments of approximately the desired size are isolated by fractionation methods known in the art, such as column chromatography or electrophoresis through a gel. As described previously, such fragments can be, for example, from about 4 to about 1000 nucleotides in length.

Subregions of the genome are particular useful in applications where it is desirable to identify cis acting nucleic acid elements that regulate genes or gene families known or predicted to be involved in growth, development or pathogenesis. Therefore, a source of double-stranded DNA that can be fragmented to form a diverse population of isolated nucleic acid molecules can be, for example, genomic DNA or a fragment therefrom, such as a chromosome or chromosomal arm, one or more DNA structural or transcriptional domains, or one or more genes. Methods of isolating such DNA preparations are known in the art. A source of single-stranded DNA can be, for example, any of the above double-stranded DNAs that either prior to or after fragmenting has been denatured by methods known in the art, including heating and alkali treatment. Similarly, sources of RNA, such as hnRNA, mRNA and viral RNA can be produced and fragmented or fractionated by means known in the art. If desired, known nucleic acid sequences can be attached to one or both ends of the isolated nucleic acid molecules.

A diverse population of isolated nucleic acid molecules of various lengths and sequence compositions can also be produced by synthetic means. For example, single-stranded DNA or RNA molecules can be synthesized using automatic nucleic acid synthesizers. Such molecules can include predetermined degenerate or random sequences at all or some positions. Methods of synthesis that result in random, degenerate or partially degenerate nucleic acid sequences are known in the art (see, for example, U.S. Pat. No. 5,723,323, incorporated herein by reference). If desired, known nucleic acid sequences can be attached to one or both ends of the isolated nucleic acid molecules. Depending on the need, single-stranded nucleic acids can be rendered double-stranded and purified by means known in the art.

The size of the diverse population of isolated nucleic acid molecules can vary depending on the need and desired efficiency for identifying a particular cis acting nucleic acid element. The larger and more diverse the population, the greater the probability of obtaining productive interactions and, therefore, the greater the likelihood of obtaining one, or many, cis acting nucleic acid elements. It is not necessary, however, to use large diverse populations to practice the methods of the invention. For example, populations of isolated nucleic acid molecules that are smaller in size or diversity but which are known or expected to contain cis acting nucleic acid elements can similarly be used and result in the identification of cis acting nucleic acid elements. For example, it is possible to identify cis acting nucleic acid elements from a population as small as two nucleic acids. Those skilled in the art will know, or can easily determine, the size and diversity of the population of isolated nucleic acid molecules to be used depending on the desired number and types of cis acting nucleic acid elements to be identified.

A population of at least about $10^{13}$ different nucleic acids that includes all possible molecules of between 5 and 20 nucleotides in length can readily be obtained by synthetic means. For example, by synthesizing oligonucleotides having each of the four naturally-occurring nucleotides at each position, a diverse population of approximately $4^5+4^6+4^7+ \ldots 4^{20}$ or approximately $10^{13}$ different candidate sequences can be obtained. Such a population would include virtually every possible sequence of between 5 and 20 nucleotides in length, including virtually every possible cis acting nucleic acid element of between 5 and 20 nucleotides in length.

Longer nucleic acid sequences can also be directly synthesized, or can be generated by combining shorter sequences. Methods of combining shorter sequences are known in the art. For example, single-stranded nucleic acids with regions of complementarity can be allowed to anneal under annealing conditions known in the art. A polymerization reaction can then be performed to extend each strand of the oligonucleotide using the overhanging portion of the complementary strand as a template. Optionally, the strands can be separated, reannealed, and extension repeated until a diverse population of the desired length is achieved.

As a further example, multiple short double stranded DNA sequences can be combined to form longer sequences using enzymatic methods known in the art. If desired, restriction enzyme sites can be designed in the flanking sequences or within the nucleic acids containing the potential cis acting nucleic acid elements. Following restriction digestion, random combinations of nucleic acid sequences can be ligated together in a ligation reaction. Alternatively, random combinations of double-stranded nucleic acids with blunt ends can be ligated together in a ligation reaction.

If desired, the isolated nucleic acid molecules can be flanked on one or both sides with nucleic acid sequences with desired properties. For example, an isolated nucleic acid molecule can have a restriction enzyme binding consensus sequence or a sequence complementary to a primer for amplification by the polymerase chain reaction (PCR) at one or both ends. These flanking nucleic acid sequences can be used, for example, to combine or extend nucleic acids as described above, to amplify nucleic acids sequences by PCR either before or after incubation with nucleic acid binding factors, or to identify or isolate nucleic acids that selectively bind to nucleic acid binding factors or compounds.

A diverse population of nucleic acid binding factors is also provided, and is used to contact the diverse population of isolated nucleic acid molecules. Depending on need, the diverse population of nucleic acid binding factors can vary in size and diversity. The larger and more diverse the population, the greater the probability of obtaining productive interactions and, therefore, the greater the likelihood of obtaining one, or many cis acting nucleic acid elements bound to nucleic acid binding factors. It is not necessary, however, to use large diverse populations to practice the methods of the invention. For example, nucleic acid binding factor populations that are smaller in size or diversity but which are known or expected to contain nucleic acid binding factors can similarly be used. Using a population containing as few as two nucleic acid binding factors in the methods of the invention, it is possible to identify one or more cis acting nucleic acid elements. Those skilled in the art will know, or can easily determine, the size and diversity of the nucleic acid binding factor population to be used depending on the desired number and types of cis acting nucleic acid elements and nucleic acid binding factors to be identified.

Depending on need, such as, for example, the type of cis acting nucleic acid element and nucleic acid binding factor one intends to identify, the population of nucleic acid binding factors can be biased to include, for example, nucleic acid binding factors that normally bind to particular types of cis acting nucleic acid elements, that are normally found in particular cell types, that respond to particular extracellular stimuli, or that are localized to particular chromosomal or subchromosomal locations.

A source of nucleic acid binding factors can be, for example, a cell or subcellular extract obtained by biochemical fractionation procedures known in the art. A cytoplasmic extract, for example, can be a source of a diverse population of nucleic acid binding factors that bind, for example, mRNA including, for example, nucleic acid binding factors involved in genetic processes such as translation, editing, degradation, and the like. A nuclear extract, for example, can be a source of a diverse population of nucleic acid binding factors that bind, for example, hnRNA and single- and double-stranded nuclear DNA including, for example, replication factors, transcription factors, splicing factors and boundary element binding factors. A mitochondrial extract can be a source of a diverse population of nucleic acid binding factors that bind, for example, mitochondrial DNA. A chloroplast extract can be a source of a diverse population of nucleic acid binding factors that bind, for example, chloroplast DNA.

A source of nucleic acid binding factors can also be nucleic acid binding factors bound to nucleic acids, either within a cell or obtained from a cell. For example, a source of nucleic acid binding factors can be cytoplasmic, mitochondrial or nuclear RNA or DNA. A source of nucleic acid binding factors can also be a preparation of nucleic acids bound to nucleic acid binding factors that is isolated from other cellular components. For example, where it is desirable to identify cis acting nucleic acid elements involved in a particular disease or developmental state, nucleic acid binding factors bound to nucleic acids from a particular genomic or chromosomal location known to be involved in the disease can be used as a source of binding factors. Therefore, a diverse population of nucleic acid binding factors bound to nucleic acids can be, for example, bound to chromatin, a chromosome, a chromosome arm, a transcriptional domain, a gene family or a gene, depending on the application of the method. A transcriptional domain refers to a loop or segment of DNA that extrudes from chromomeres and that is bounded by cis acting boundary elements. Such a structural domain is often an actively transcribed region of DNA.

If desired, nucleic acid binding factors can be released from a nucleic acid preparation and used to contact the diverse population of isolated nucleic acid molecules. Methods of releasing nucleic acid binding factors bound to a nucleic acid in a nucleic acid preparation can be determined for a particular nucleic acid preparation by those skilled in the art and include, for example, varying the salt concentration or pH of the solution.

Diverse populations of nucleic acid binding factors can also be obtained by recombinant methodologies. One skilled in the art would be able to determine an appropriate source of nucleic acids to express to obtain nucleic acid binding factors for a particular application of the method. For example, cDNA libraries are available or can be produced by known methods from genes expressed by any desired tissue or cell source, or in response to any pathogenic or normal stimulus.

Depending on the types of cis acting nucleic acid elements one wishes to identify, nucleic acid binding factors can be obtained as described above from cells from different tissues or at different developmental stages. Nucleic acid binding factors can also be obtained from either normal or diseased cells, or following exposure of cells to external stimuli such as therapeutic drugs.

Once the starting populations of isolated nucleic acid molecules and nucleic acid binding factors have been selected and obtained, the populations are combined under conditions that allow the nucleic acid binding factors to selectively bind to the isolated nucleic acid molecules containing cis acting nucleic acid elements. Binding conditions will vary depending on the type and source of nucleic acid binding factors and the type and source of nucleic acids, but can be readily determined. For example, since the affinity and specificity of interactions between nucleic acid binding factors and cis acting nucleic acid elements are generally dependent on the charge of both molecules, one can vary the salt concentration or pH of a buffer to differentially allow binding interactions of particular affinities.

Conditions that allow binding between nucleic acid sequences and nucleic acid binding factors are also designed to ensure that a sufficient concentration of nucleic acids and nucleic acid binding factors are present for a particular application. For example, in one embodiment of the invention, nucleic acid binding factors bound to nucleic acids in a nucleic acid preparation are contacted with a diverse population of isolated nucleic acids. The nucleic acid binding factors will equilibrate between being bound to the cis acting nucleic acid elements present in the nucleic acid preparation, and the cis acting nucleic acid elements present in the diverse population of isolated nucleic acid molecules. The distribution of nucleic acid binding factors between being bound to cis acting nucleic acid elements present in the nucleic acid preparation, and being bound to cis acting nucleic acid elements in the isolated population of nucleic acids will depend, for example, on the ratio between the number of copies of the corresponding cis acting nucleic acid elements present in the nucleic acid preparation and the number of copies of the corresponding cis acting nucleic acid elements in the isolated population. An excess of a particular isolated cis acting nucleic acid element to a cis acting nucleic acid element present in the nucleic acid preparation would shift the binding equilibrium toward preferential binding to the isolated nucleic acid molecules. For example, an excess of about 10 to 1, or about $10^3$ to 1, or about $10^4$ to $10^{10}$ to 1 of isolated cis acting nucleic acid elements to cis acting nucleic acid element present in the nucleic acid preparation could be used in the invention. However, smaller ratios can also be used without substantially reducing the selectivity of the interaction. The use of smaller ratios, including, for example, equal amounts or less than an excess of isolated cis acting nucleic acid elements compared to those in the preparation can be advantageous, for example, when selectively identifying high affinity interactions between the cis acting nucleic acid element and nucleic acid binding factors.

As an example, if a chromatin preparation is contacted with a diverse population of isolated nucleic acid molecules, the number of isolated nucleic acid molecules is chosen so as to compete with the chromatin for the chromatin-bound factors to a desired extent for a particular application. One skilled in the art could determine the number of copies of each member of the diverse population of isolated nucleic acid molecules required for a particular application of the method. Methods known in the art, such as the polymerase chain reaction, allow production of as many copies of a particular isolated nucleic acid sequence as desired.

After allowing isolated nucleic acid molecules to contact and bind nucleic acid binding factors, nucleic acids that selectively bind to nucleic acid binding factors are identified. These nucleic acids contain one or more cis acting nucleic acid elements. Any method for identifying nucleic acids that are selectively bound to nucleic acid binding factors can be used, including methods of physically separating bound and unbound nucleic acids, as well as methods of distinguishing between bound and unbound nucleic acids that do not require the physical separation of bound from unbound nucleic acids.

Methods of physically separating nucleic acids that are bound to binding factors from nucleic acids that are unbound are known in the art. For example, nucleic acids that are bound to nucleic acid binding factors and those that are unbound can be separated by virtue of size, shape, charge or density of the bound complex as compared to unbound nucleic acids. For example, nucleic acids bound to nucleic acid binding factors will pass through a chromatography column at a different rate than unbound nucleic acids. Appropriate chromatography resins can be determined by those skilled in the art for a particular application. Additionally, depending on the nature of the nucleic acid binding factor, a nucleic acid bound to a nucleic acid binding factor can have a greater or lesser density than an unbound nucleic acid, and can be separated from unbound nucleic acids by known methods of density centrifugation. Furthermore, bound and unbound nucleic acids will have different electrophoretic mobilities, and can be separated by methods known in the art such as electrophoretic mobility shift assays (EMSA). If desired, the bound nucleic acids can be isolated, stored, amplified, sequenced or used as described below.

Furthermore, it is known that a nitrocellulose membrane will selectively retain double-stranded DNA bound to proteinaceous nucleic acid binding factors, but will allow unbound DNA to pass through the filter. Therefore, following binding of isolated nucleic acid molecules with nucleic acid binding factors, the binding reaction can be filtered through a nitrocellulose filter. DNAs that are bound to nucleic acid binding factors are retained on a nitrocellulose filter. These DNAs contain cis acting nucleic acid elements. If desired, the retained nucleic acids can be eluted from the nitrocellulose membrane and stored, amplified, sequenced or used as described below. One skilled in the art can also vary buffer conditions to selectively retain single-stranded nucleic acid sequences bound to nucleic acid binding factors on nitrocellulose filters while allowing unbound nucleic acid sequences to pass through the filters. The retained nucleic acids contain cis acting nucleic acid elements. One skilled in the art could also modify such as assay by, for example, varying the type of membrane, to selectively retain nucleic acids bound to non-proteinaceous nucleic acid binding factors.

Methods of distinguishing between nucleic acids that are bound to nucleic acid binding factors and those that are unbound, which do not require the physical separation of bound from unbound nucleic acids, are similarly known in the art. A method of distinguishing between bound nucleic acids and unbound nucleic acids takes advantage of properties that distinguish bound nucleic acids as compared to unbound nucleic acids such as, for example, nuclease resistance. As one example of the use of nuclease resistance to distinguish bound from unbound nucleic acids, a diverse population of isolated double-stranded DNA can be flanked, at one or both ends, with a sequence containing the binding site of a restriction enzyme that is known, or can be designed, to cut at a site at a distance away from the binding site. Both ends of the nucleic acid also contain sequences that are complementary to PCR primers. Following binding between isolated nucleic acid molecules and nucleic acid binding factors, the reaction mixture is further incubated with such a restriction enzyme under conditions that allow cleavage of DNA at the restriction enzyme cleavage site only if the cleavage site is not bound to a nucleic acid binding factor. Thus, DNA that is unbound is cleaved, and bound DNA is not cleaved. Uncleaved DNA therefore retains PCR primer sites at both ends of the cis acting nucleic acid element and can be amplified by PCR, whereas cleaved DNA only has a single primer site and can not be amplified by PCR. If desired, the nucleic acid binding factor and restriction enzyme can be removed by methods known in the art, such as by appropriately varying the buffer conditions. A PCR reaction is then performed, which amplifies only those nucleic acids that were bound to nucleic acid binding factors. These nucleic acids contain cis acting nucleic acid elements.

Restriction enzymes that cleave at a distance of about 5 to about 30 nucleotides away from the binding site are commercially available. Such enzymes include, for example, BbvI, BcgI, BciVI, BpmI, BseRI, BsmFI, FokI, HgaI, HphI, MboII, MnlI and SfaNI, each of which is available from New England BioLabs, Inc. Using knowledge of restriction enzyme structure, it is also possible to design restriction enzymes that combine a desired binding site specificity with a desired cleavage site specificity and cleavage site distance.

For certain methods of distinguishing between bound and unbound nucleic acids, it may be desirable to detectably label either the diverse population of nucleic acids or the diverse population of nucleic acid binding factors. Detectable labels include moieties such as, for example, enzymes, radioisotopes, fluorochromes, chemiluminescent markers, and biotin, which can be incorporated into isolated nucleic acid molecules and nucleic acid binding factors, or incorporated by metabolic labeling into nucleic acids and nucleic acid binding factors in vivo or in cultured cells. A detectable label can also be a tag that can be specifically recognized by a binding moiety, such as, for example, an antibody.

For certain applications of the method, such as high-throughput screening for therapeutic compounds and for diagnostic procedures, it is advantageous to provide the diverse population of nucleic acids on a solid support. The diverse population of nucleic acids can be synthesized on, or subsequently attached to, solid supports such as beads, pins, resins or chips. Nucleic acids attached to solid supports can be contacted with nucleic acid binding factors; those nucleic acid binding factors that are not specifically bound to nucleic acids are removed, and the nucleic acids, both bound and unbound, remain attached to the solid support. The bound nucleic acids can be detected, for example, by virtue of the detectable label present in either the nucleic acid or the nucleic acid binding factor, or by virtue of another inherent detectable property, such as charge, size or nuclease resistance, that distinguishes bound from unbound nucleic acids.

For example, the fluorescence of a fluorescently labeled nucleic acid can be quenched by binding to a nucleic acid binding factor, and this quenching can be detected. Similarly, the amount of chemiluminescent signal or radioactivity of a nucleic acid that can be detected can be altered by binding to a nucleic acid binding factor. Additionally, binding of nucleic acid binding factor can protect a nucleic acid from degradation by nucleases, and the undegraded nucleic acids can be detected by virtue of their detectable labels.

It is not necessary to be able to directly isolate a nucleic acid that is bound to a nucleic acid binding factor in order to identify it, if the corresponding sequence of the nucleic acid that was bound to the binding factor is known. For example, nucleic acids can be synthesized on solid supports in arrays, with nucleic acids of known sequences present at known locations. Therefore, any property that identifies selectively bound nucleic acids from unbound nucleic acids in a diverse population of nucleic acids present in an array of nucleic acids can be used to identify cis acting nucleic acid elements. Nucleic acid chips and automated detection procedures are particularly advantageous in high-throughput screening procedures for identifying cis acting nucleic acid elements, nucleic acid binding factors, and compounds that bind cis acting nucleic acid elements and nucleic acid binding factors.

Solid phase oligonucleotide synthesis methods are known in the art (see, for example, J. Weiler et al., *Anal. Biochem.*

243:218 (1996) and U. Maskos et al., *Nucleic Acids Res.* 20(7):1679 (1992); T. Atkinson et al., *Solid-Phase Synthesis of Oligodeoxyribonucleotides by the Phosphitetriester Method, in Oligonucleotide Synthesis* 35 (M. J. Gait ed., 1984), as are methods for synthesizing arrays of oligonucleotides (see, for example, U.S. Pat. No. 5,474,796; International Publication No. WO 95/25116; Blanchard et al., "High-density oligonucleotide arrays" *Biosensors & Bioelectronics* 11(6/7):687–690 (1996)).

The above methods of distinguishing between nucleic acids that are bound to nucleic acid binding factors and those that are not can be used individually, or in any combination or order, to identify nucleic acids containing cis acting nucleic acid elements.

Once the sequences of one or a plurality of isolated nucleic acid molecules containing cis acting nucleic acid elements is determined, any desired set or subset thereof can be synthesized, using methods known in the art, and used in a variety of therapeutic, diagnostic and screening methods. The cis acting nucleic acid elements within the isolated nucleic acid molecules can be determined, if desired, by means known in the art. For example, known methods of nucleic acid "footprinting" can be used. A nucleic acid can be detectably labeled and contacted with a nucleic acid binding factor or population of nucleic acid binding factors. The nucleic acid is then partially digested with a nuclease. The sequences that are protected from nuclease digestion by the bound nucleic acid binding factor are the cis acting nucleic acid elements.

If desired, the sequences of isolated cis acting nucleic acid elements identified by a method of the invention can be directly compared with cis acting nucleic acid elements found in cellular or viral DNA or RNA. Such comparison is advantageous, for example, in determining the extent to which a cis acting nucleic acid element identified by a method of the invention is identical to a cis acting nucleic acid element found in naturally occurring populations of nucleic acids. Such comparison also advantageously allow the determination of which nucleic acids are regulated by particular cis acting nucleic acid elements. These regulated nucleic acids can include previously unknown or uncharacterized genes involved in disease or development, which can themselves be used in therapeutic and diagnostic procedures.

Several methods are known in the art that can be used to compare sequences of isolated cis acting nucleic acid elements to cis acting nucleic acid elements found in cellular or viral DNA or RNA. For example, the partial or complete genomic sequences of a variety of different organisms, including humans, are available in databases. These databases can be searched for identical or substantially similar sequences to the cis acting nucleic acid elements identified by a method of the invention. The regulated genes can be identified and produced by recombinant or synthetic means known in the art.

Additionally, populations of nucleic acids cloned in, for example, phage, plasmid, cosmid or YAC libraries are available or can be prepared by methods known in the art. These libraries can be screened using methods known in the art, such as nucleic acid hybridization, to determine the cis acting nucleic acid elements and flanking sequences in the cellular or viral nucleic acids that are substantially similar to the cis acting nucleic acid elements identified by the methods of the invention.

Furthermore, the location of one or a plurality of cis acting nucleic acid elements within a particular cell compartment or within a particular chromosome can be advantageously used to characterize the cis acting nucleic acid elements and the nucleic acids they regulate. For example, depending on the starting population of isolated nucleic acid molecules and nucleic acid binding factors, several types of cis acting nucleic acid elements could be simultaneously identified. Therefore, by examining the location of hybridization of a cis acting nucleic acid element to the cellular nucleic acids, the type of cis acting nucleic acid element and the location of the regulated nucleic acids can be determined. For example, boundary elements, elements that bind telomeres and elements that bind transcription factors could be distinguished by knowing where each element mapped to the chromosomes. Similarly, RNA elements that are present in mRNA as compared to hnRNA could be distinguished by virtue of their intracellular location. Such methods of mapping nucleic acid sequences to particular nucleic acid locations are known in the art and include, for example, fluorescence in situ hybridization (FISH).

The methods of the invention for identifying and isolating cis acting nucleic acid elements that are bound to nucleic acid binding factors also simultaneously provide for the identification and isolation of nucleic acid binding factors that selectively bind cis acting nucleic acid elements. Therefore, the invention provides a method of isolating a nucleic acid binding factor. The method involves contacting a diverse population of nucleic acid binding factors with a diverse population of isolated nucleic acid molecules under conditions that allow nucleic acid binding factors to selectively bind nucleic acids, and isolating one or more nucleic acid binding factors that selectively bind one or more isolated nucleic acid molecules. The source and diversity of the populations of nucleic acid binding factors and isolated nucleic acid molecules can be determined by those skilled in the art, as described previously, based on the type and number of nucleic acid binding factors that it is desired to isolate in a particular application of the method.

Following contacting the populations of isolated nucleic acid molecules and nucleic acid binding factors, the isolated nucleic acid molecules that are selectively bound by nucleic acid binding factors are separated from unbound nucleic acids. As described previously, methods are known in the art to physically separate nucleic acids that are bound to nucleic acid binding factors from nucleic acids that are unbound. Such methods include, for example, filtration, chromatography, electrophoresis and centrifugation. The selectively bound nucleic acid binding factors are dissociated from the nucleic acids they bind and are isolated. Methods of dissociating nucleic acid binding factors from nucleic acids are known in the art and include, for example, varying the salt or detergent concentration or the pH of the buffer.

Once isolated, the nucleic acid binding factor of interest can be produced in large quantity from a diverse population of nucleic acid binding factors using, for example, its corresponding cis acting nucleic acid element or other binding agent, such as a specific antibody, as an affinity reagent. Furthermore, if a nucleic acid binding factor is a protein, the sequence of the encoding gene can be readily determined and the nucleic acid binding factor can be recombinantly produced.

The site of interaction between a nucleic acid binding factor and other binding factors in a binding complex, and the site of interaction between a nucleic acid binding factor and its corresponding cis acting nucleic acid element, also can be determined using methods known in the art. Knowledge about these sites of interaction can be used to design therapeutic compounds that alter or disrupt these interactions.

The genetic circuitry of cells and viruses controls cell and organismal behavior, including, for example, proliferation, differentiation and pathogenicity. Therefore, being able to modulate the control properties, dynamics or behavior of the genetic circuitry or to modify the genetic circuitry directly, of a host cell or a pathogen in a controlled way, in order to alter nucleic acids that mediate these processes, can be advantageous for therapy. For example, modulating the control properties, dynamics or behavior of the genetic circuitry of a cell, or modifying the genetic circuitry directly, can be used to modulate the proliferation, differentiation, susceptibility to disease or susceptibility to drugs of the cell, depending on the particular therapeutic application. Modulating the control properties, dynamics or behavior of the genetic circuitry of a pathogen, or modifying its genetic circuitry directly, can also be used to modulate the infectivity, pathogenicity or drug resistance of the pathogen.

The identification of cis acting nucleic acid elements and nucleic acid binding factors provides a means of rapidly identifying compounds that can alter the control properties, dynamics or behavior of the genetic circuitry of a cell or virus for therapeutic purposes. The identification of cis acting nucleic acid elements that modulate a genetic activity of nucleic acids involved in a pathological condition also provides a means of inserting, removing or replacing the cis acting nucleic acid elements to directly modify the genetic circuitry of a cell for therapeutic purposes.

The methods of the invention provide for the identification of therapeutic compounds that can target any nucleic acid or group of nucleic acids of interest that contain one or more cis acting nucleic acid elements. Such therapeutic compounds include, for example, analogs of cis acting nucleic acid elements, analogs of nucleic acid binding factors, compounds that bind to either cis acting nucleic acid elements or nucleic acid binding factors or both, as well as cis acting nucleic acids and nucleic acid binding factors themselves. These therapeutic compounds can, for example, compete with an endogenous cis acting nucleic acid element for binding to a nucleic acid binding factor, or compete with a nucleic acid binding factor for binding with its corresponding cis acting nucleic acid element. These compounds can also physically disrupt the binding of an endogenous cis acting nucleic acid element to its corresponding nucleic acid binding factor or disrupt the binding between two or more nucleic acid binding factors.

Altering the regulation of nucleic acids associated with disease can prevent or treat disease. Compounds that target cis acting nucleic acid elements and nucleic acid binding factors involved in particular diseases can be identified and used to enhance, inhibit, alter, antagonize or mimic the regulation of a nucleic acid known or predicted to be associated with disease. For example, cis acting nucleic acid elements or nucleic acid binding factors that are known or expected to modulate one or a plurality of nucleic acids involved in cancer, degenerative diseases, genetic disorders, immune disorders, bacterial and viral infectious diseases and the like, can be used in the methods described below to identify specific therapeutic compounds that will target the corresponding regulated nucleic acid. These therapeutic compounds can beneficially alter a genetic activity of the nucleic acid, such as, for example, its structural integrity, transcription, translation, or replication, so as to ameliorate or prevent the disease.

The isolated nucleic acid molecules or the nucleic acid binding factors, or both, in the exemplary methods of identifying therapeutic compounds described below, can be biased populations that include cis acting nucleic acid elements or nucleic acid binding factors that are known or predicted to regulate nucleic acids involved in a disease. The compounds so obtained would be expected to preferentially include compounds that are selective for the nucleic acids involved in the particular disease. Alternatively, the starting populations can be large, random populations of nucleic acids and nucleic acid binding factors. In the latter case, it would be expected that a library of compounds would be obtained, only a few of which would be selective for any particular nucleic acid or nucleic acid binding factor. However, the library of compounds obtained using the methods of the invention can readily be screened to determine which subset of compounds alters the regulation of any nucleic acid of interest.

Methods of screening to determine that a compound alters the regulation of a particular nucleic acid can be determined by those skilled in the art depending on the nucleic acid and its properties. For example, the affinity and selectivity of a compound for binding to a particular cis acting nucleic acid element or nucleic acid binding factor could be determined using a binding competition assay. Likewise, the effect of a compound on the regulation of a nucleic acid could be determined by examining the expression of the mRNA or protein encoded by the regulated nucleic acid. Furthermore, the effect of the compound on a property of a cell, such as growth, differentiation or apoptosis, that depends on the expression of the gene, could be determined.

Compounds that selectively bind to nucleic acid binding factors, such that they can be selectively displaced by isolated nucleic acid molecules, are analogs of cis acting nucleic acid elements. Such compounds are potential therapeutic agents that can alter a genetic activity modulated by a cis acting nucleic acid element of which the compound is an analog. Therefore, the invention provides a method of identifying a cis acting nucleic acid element analog. The method involves contacting a diverse population of nucleic acid binding factors with a diverse population of compounds under conditions that allow the compounds to selectively bind the nucleic acid binding factors. One or more of the nucleic acid binding factors selectively bound to one or more of the compounds is contacted with one or more isolated nucleic acid molecules under conditions that allow one or more of the isolated nucleic acid molecules to selectively displace one or more of the selectively bound compounds. The isolated nucleic acid molecules or the nucleic acid binding factors, or both, can correspond to or regulate nucleic acids that are known or expected to play a role in a disease of interest. The displaced compounds are identified and characterized as cis acting nucleic acid element analogs. Such a method further provides for the identification of one or more of the isolated nucleic acid molecules that selectively displaces one or more of the selectively bound compounds. An isolated nucleic acid molecule that selectively displaces one or more of the selectively bound compounds is characterized as a nucleic acid containing a cis acting nucleic acid element.

Compounds that selectively bind to isolated nucleic acid molecules or to nucleic acid binding factors in a nucleic acid binding factor complex, such that they can be displaced by selectively binding to nucleic acid binding factors, are analogs of nucleic acid binding factors. Such compounds are potential therapeutic agents that can alter a genetic activity modulated by a cis acting nucleic acid element that binds a nucleic acid binding factor of which the compound is an analog. Therefore, the invention also provides a method of identifying nucleic acid binding factor analogs. In one embodiment, the method consists of contacting a diverse population of compounds with a diverse population of isolated nucleic acid molecules under conditions that allow the compounds to selectively bind the isolated nucleic acid molecules. One or more of the isolated nucleic acid molecules selectively bound to one or more of the compounds is contacted with one or more nucleic acid binding factors under conditions that selectively displace one or more of the selectively bound compounds from one or more of the bound nucleic acids. The isolated nucleic acid molecules or the nucleic acid binding factors, or both, can correspond to or regulate nucleic acids that are known or expected to play a role in a disease of interest. The displaced compounds are identified, and are characterized as nucleic acid binding factor analogs. The method further provides for the identification of one or more nucleic acid binding factors that displaces one or more of the selectively bound compounds.

In a further embodiment of the above method, compounds that selectively bind either to cis acting nucleic acid elements or to nucleic acid binding factors in a nucleic acid binding factor complex or to both can be simultaneously identified. The method involves contacting a diverse population of compounds with a diverse population of isolated nucleic acid molecules bound to nucleic acid binding factors under conditions that allow the compounds to selectively bind to either the isolated nucleic acid molecules or to the nucleic acid binding factors. One or more of the isolated nucleic acid molecules selectively bound to nucleic acid binding factors and selectively bound to one or more compounds is contacted with one or more nucleic acid binding factors under conditions that allow one or more of the nucleic acid binding factors to selectively displace one or more of the selectively bound compounds. The isolated nucleic acid molecules or the nucleic acid binding factors, or both, can correspond to or regulate nucleic acids that are known or expected to play a role in a disease of interest. The displaced compounds are identified, and are characterized as nucleic acid binding factor analogs. The displaced compounds can further be characterized to determine whether they bind to a cis acting nucleic acid element or to a nucleic acid binding factor in a complex of nucleic acid binding factors.

Compounds that selectively bind to cis acting nucleic acid elements can also be used as therapeutic agents to alter the activity of nucleic acids modulated by cis acting nucleic acid elements. Therefore, the invention also provides a method of identifying compounds that bind cis acting nucleic acid elements. The method involves contacting a plurality of isolated nucleic acid molecules, wherein each nucleic acid comprises one or more cis acting nucleic acid elements, with a diverse population of compounds under conditions that allow the compounds to selectively bind the isolated nucleic acid molecules. The compounds that selectively bind one or more isolated nucleic acid molecules containing one or more cis acting nucleic acid elements are identified.

As described previously, the isolated nucleic acid molecules containing cis acting nucleic acid elements can correspond to nucleic acids that are known or expected to play a role in a disease of interest, or can be a large, random population. A compound identified by the method can be tested for its ability to bind a cis acting nucleic acid element of interest by direct or indirect assays known in the art. Such assays include, for example, binding assays, reporter assays, and functional assays that measure the effect of introduction of the compound on a property of the cell.

The invention also provides a method of identifying compounds that selectively displace binding of a cis acting nucleic acid element to a nucleic acid binding factor or of a nucleic acid binding factor to another nucleic acid binding factor. The method involves contacting a plurality of isolated nucleic acid molecules selectively bound to nucleic acid binding factors, with a diverse population of compounds under conditions that allow the compounds to selectively displace one or more of the selectively bound nucleic acid binding factors from one or more of the bound nucleic acids or from one or more of the bound nucleic acid binding factors in the binding factor complex. The isolated nucleic acid molecules containing cis acting nucleic acid elements or the nucleic acid binding factors, or both, can correspond to or regulate nucleic acids that are known or expected to play a role in a disease of interest. The isolated nucleic acid molecules can be selected to each contain one or more cis acting nucleic acid elements. The compounds that selectively displace one or more of the bound nucleic acid binding factors from one or more of the bound nucleic acids or from one or more of the bound nucleic acid binding factors in the binding factor complex are identified. Such a compound can, for example, bind to the site of interaction between the cis acting nucleic acid element and the nucleic acid binding factor and be, therefore, either a cis acting nucleic acid element analog or a nucleic acid binding factor analog. Such a compound can also, for example, bind to the site of interaction between two or more nucleic acid binding factors within a nucleic acid binding factor complex. Alternatively, such a compound can bind elsewhere on the cis acting nucleic acid element or elsewhere on one or more of the nucleic acid binding factors, so long as binding between a nucleic acid binding factor and either a cis acting nucleic acid element or another nucleic acid binding factor is selectively modified or displaced by binding of the compound.

The methods of the invention described above can be used to identify compounds that are selective for many different nucleic acids as well as compounds that target only a very limited number of nucleic acids. As described previously, some of the cis acting nucleic acid elements that regulate a particular nucleic acid will likely also be involved in the regulation of numerous other nucleic acids. Therefore, a therapeutic compound that binds to that cis acting nucleic acid element or its corresponding nucleic acid binding factor may have an effect on the regulation of many nucleic acids other than the intended target nucleic acid. However, a particular combination of cis acting nucleic acid elements will be relatively specific for a particular nucleic acid or family of nucleic acids. Therefore, the invention also provides for the identification of therapeutic agents that are specific for one or several nucleic acids by using isolated nucleic acid molecules that include a combination of cis acting nucleic acid elements in the methods described above. The cis acting nucleic acid elements in the combination of cis acting nucleic acid elements can be linked by the naturally occurring intervening sequences. Alternatively, so as to provide for a convenient overall nucleic acid length, non-native intervening sequences can be introduced between the cis acting nucleic acid elements. Using the methods described above, therapeutic compounds that selectively bind to the combination of cis acting nucleic acid elements, or compounds that selectively bind to or displace the combination of nucleic acid binding factors, can be identified.

The above methods of identifying compounds that can be used as therapeutic agents take advantage of the ability to distinguish between nucleic acids that are selectively bound to particular compounds or binding factors, and nucleic acids that are either unbound or bound to different compounds or binding factors. Any method of distinguishing bound from unbound nucleic acids can be used in the above methods of identifying therapeutic compounds that bind cis acting nucleic acid elements and nucleic acid binding factors, such as those described previously. Such methods can be automated by, for example, providing arrays of isolated nucleic acid molecules on solid supports. Similarly, arrays of compounds on solid supports can be provided. The compounds, the nucleic acid binding factors, or the nucleic acids can be detectably labeled by methods known in the art. Additionally, isolated nucleic acid molecules that are bound to particular compounds can differ from unbound nucleic acids or nucleic acids bound to different compounds or nucleic acid binding factors in their ability to be retained on filters such as nitrocellulose filters, and can differ in charge, size, density, electrophoretic mobility and resistance to nucleases.

Compounds, nucleic acid binding factors, and isolated nucleic acids can be removed from the molecules they selectively bind for further characterization, if desired. Alternatively, pools of such molecules can be repeatedly subdivided until one or a plurality of selectively bound or selectively displaced molecules is isolated or identified.

The invention also provides a plurality of isolated nucleic acid molecules, wherein each isolated nucleic acid molecule contains one or more cis acting nucleic acid elements. Such a plurality of isolated nucleic acid molecules containing cis acting nucleic acid elements can contain, for example, between about 2–5 different isolated nucleic acid molecules, or between about 6–10 different isolated nucleic acid molecules.

The plurality of isolated nucleic acids can also contain between about 11–20 different isolated nucleic acid molecules or greater than about 20 different isolated nucleic acid molecules. The number of isolated nucleic acid molecules will depend on the type of nucleic acids in the plurality and the intended use of the plurality. These nucleic acids can be attached to a solid support, if desired, and advantageously used for automated screening and diagnostic procedures.

A plurality of isolated nucleic acid molecules containing cis acting nucleic acid elements can be identified and obtained, for example, by the methods described above. The plurality can be produced in abundance by, for example, chemical synthesis or by amplification by the polymerase chain reaction. If desired, isolated cis acting nucleic acid elements can be synthesized with various amounts of adjacent sequences. These adjacent sequences can be used, for example, in the detection, amplification, cloning or further modification of the sequences. As described above, a plurality of isolated nucleic acid molecules containing cis acting nucleic acid elements can be, for example, a set of isolated transcription factor binding elements, such as enhancers and promoters; a set of isolated replication factor binding elements, such as origins of replication; a set of isolated restriction or modification enzyme binding sites; or any other set of nucleic acid cis acting elements that regulates a desired genetic activity of nucleic acids.

As described above, a plurality of isolated nucleic acid molecules containing cis acting nucleic acid elements can be characteristic of, for example, a particular cell type, a particular disease or developmental state of a cell, or a particular response to external stimuli. A plurality of nucleic acids containing cis acting nucleic acid elements can also be characteristic of a particular subset of cellular nucleic acids, such as a chromosomal region that maps to a disease locus.

The invention also provides a plurality of isolated nucleic acid molecules bound to nucleic acid binding factors, wherein each isolated nucleic acid molecule contains one or more cis acting nucleic acid elements. Such a plurality of isolated nucleic acid molecules bound to nucleic acid binding factors can contain, for example, between about 2–5 different isolated nucleic acid molecules, or between about 6–10 different isolated nucleic acid molecules. The plurality of isolated nucleic acids can also contain between about 11–20 different isolated nucleic acid molecules or greater than about 20 different isolated nucleic acid molecules. The number of isolated nucleic acid molecules bound to nucleic acid binding factors will depend on the type of nucleic acids and nucleic acid binding factors in the plurality and the intended use of the plurality. These nucleic acids or nucleic acid binding factors can be attached to a solid support, if desired, and advantageously used for automated screening and diagnostic procedures. As described above, such a plurality can be used, for example, to identify therapeutic compounds that can selectively modify or displace the binding of a cis acting nucleic acid element to a nucleic acid binding factor or that can selectively modify or displace the binding between two or more nucleic acid binding factors.

The invention also provides a plurality of isolated nucleic acid binding factors that includes at least about 15 different isolated nucleic acid binding factors. The plurality of isolated nucleic acid binding factors can also contain between about 16–25 different isolated nucleic acid binding factors, preferably between about 26–50 different isolated nucleic acid binding factors, and more preferably greater than about 51 different isolated nucleic acid binding factors. The number of isolated nucleic acid binding factors in the plurality will depend on the type of nucleic acid binding factors in the plurality and the intended use of the plurality. If desired, the plurality of isolated nucleic acid binding factors can be attached to a solid support, and advantageously used for automated screening and diagnostic procedures.

The invention also provides a plurality of cis acting nucleic acid analogs. Such a plurality of cis acting nucleic acid analogs can include between about 2–5 different isolated cis acting nucleic acid element analogs, or between about 6–10 different isolated cis acting nucleic acid element analogs. The plurality of cis acting nucleic acid analogs can also contain, between about 11–20 different isolated cis acting nucleic acid element analogs or greater than about 20 different isolated cis acting nucleic acid element analogs. These analogs can be compounds obtained, for example, by the methods of the invention and are potential therapeutic agents that can be used to alter the interactions between the cis acting nucleic acid elements they mimic and nucleic acid binding factors.

The invention further provides a plurality of nucleic acid binding factor analogs. Such a plurality of cis acting nucleic acid analogs can include between about 2–5 different isolated cis acting nucleic acid element analogs, or between about 6–10 different isolated cis acting nucleic acid element analogs. The plurality of 20 isolated cis acting nucleic acid element analogs can also contain, between about 11–20 different isolated cis acting nucleic acid element analogs or greater than about isolated cis acting nucleic acid element analogs. These analogs can be compounds obtained, for example, by the methods of the invention and are potential therapeutic agents that can be used to alter the interactions between the nucleic acid binding factors they mimic and either cis acting nucleic acid elements or other nucleic acid binding factors within a complex of nucleic acid binding factors.

As described previously, the invention provides for the identification of cis acting nucleic acid elements and nucleic acid binding factors that regulate or modulate the genetic activity of nucleic acids that cause or are involved pathological conditions. The methods of the invention also provide for the identification of therapeutic compounds, including cis acting nucleic acid elements, nucleic acid binding factors and their analogs, that can be used therapeutically to alter the genetic activity of these nucleic acids involved in pathological conditions. Therefore, the invention provides a method of treating a pathological condition in an individual. The method involves administering to an affected individual an effective amount of one or more therapeutic agents that selectively alter the ability of one or more cis acting nucleic acid elements to regulate a genetic activity of one or more nucleic acids involved in the pathological condition.

A pathological condition mediated by the dysregulation of one or more nucleic acids can be treated by a method of the invention. For example, a therapeutic compound can be administered to either selectively increase or selectively decrease a genetic activity of one or more nucleic acids that is dysregulated in the cells of the diseased individual, as required. Similarly, a pathological condition mediated by a virus or bacteria can be treated by administering a compound that selectively alters a genetic activity of the pathogen.

The nucleic acids involved in the pathological condition are known in the art or are determined, for example, as described below using the knowledge that cis acting nucleic acid elements are present in the vicinity of actively transcribed genes. The appropriate genetic activity to target using a method of the invention can be determined by those skilled in the art and will depend on the underlying disease mechanism for a particular disease. As one example, cancer can be treated by administering a therapeutic compound of the invention that selectively targets oncogene transcription. As a further example, a viral infection can be treated by administering a compound of the invention that selectively targets viral replication.

A therapeutic agent can be formulated into a pharmaceutical composition that is convenient for delivering the agent to the target cells and to the target location within the cell, such as, for example, the nucleus or cytoplasm. Such pharmaceutical compositions contain the therapeutic agent together with a pharmaceutically acceptable carrier. Pharmaceutically acceptable carriers are well known in the art and include aqueous solutions such as water, physiologically buffered saline or other solvents or vehicles such as glycols, glycerol, oils such as olive oil or injectable organic esters and liposomes.

A pharmaceutically acceptable carrier can contain physiologically acceptable compounds that act, for example, to stabilize or increase the absorption of the therapeutic agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the nature of the therapeutic agent and on the route of administration.

The therapeutic agent also can be incorporated, if desired, into liposomes, which consist of phospholipids or other lipids, and are nontoxic, physiologically acceptable and metabolizable carriers that are relatively simple to make and administer. Targeting of a therapeutic agent encapsulated in liposomes to a cell or tissue in an individual can be passive or active. Passive targeting, for example, utilizes the tendency of liposomes to accumulate in cells of the reticuloendothelial system (RES) and in organs such as the liver, which contain sinusoidal capillaries. Active targeting, in comparison, involves alteration of the liposome by coupling a specific ligand such as a monoclonal antibody, a sugar, a glycolipid or a protein such as a ligand for a receptor expressed by the target cells.

A nucleic acid therapeutic agent, or an encoded polypeptide, can be contained in a vector known in the art, such as a plasmid, cosmid, or viral vector. Viral vectors such as retroviral vectors, adenovirus vectors, herpes simplex virus vectors, vaccinia virus and the like are particularly useful for the administration of nucleic acid therapeutic agents and encoded polypeptides. The choice of vector and route of administering the vector will depend, for example, on the particular target cells, and can be determined by those skilled in the art.

A therapeutic agent that modulates genetic activities mediated by cis acting nucleic acid elements can be administered to an individual by various routes including, for example, orally or parenterally, such as intravenously, intramuscularly, subcutaneously, intraorbitally, intracapsularly, intraperitoneally, intrarectally intracisternally or by passive or facilitated absorption through the skin using, for example, a skin patch or transdermal iontophoresis, respectively. Furthermore, a therapeutic agent can be administered by injection, intubation, orally or topically, the latter of which can be passive, for example, by direct application of an ointment or powder, or active, for example, using a nasal spray or inhalant.

Compounds identified as described above as therapeutic agents can be further modified using known methods so as to have, for example, enhanced stability or bioavailability, or to have optimal affinity for a cis acting nucleic acid element or a nucleic acid binding factor. A compound can also be modified to have positive or negative regulatory activities. For example, a compound that binds a cis acting nucleic acid element or a nucleic acid binding factor can be modified to include a transcriptional activation domain so as to selectively activate transcription of a gene. Similarly, a compound can be modified to include a domain that would, for example, cleave a nearby nucleic acid sequence or attenuate its transcription.

Identification of cis acting nucleic acid elements also allows alteration of the genetic circuitry of a cell by genetic modification. Genetic modification can be used, for example, to enhance, reduce or alter the expression of a nucleic acid or group of nucleic acids for therapeutic purposes. For example, a normal or altered copy of one or more cis acting nucleic acid elements can be introduced at a normal location or altered location within the genome of a cell, in order to modify the regulation of a nearby nucleic acid. The cis acting nucleic acid element can be, for example, responsive to an agent such as a hormone, growth factor, metal ion or antibiotic. Following insertion, the cis acting nucleic acid element confers regulation by the agent on the nucleic acid of interest. Similarly, a strong constitutive promoter or enhancer element or elements can be inserted in close proximity to a nucleic acid of interest to constitutively increase the expression of the nucleic acid. One or more cis acting nucleic acid elements that normally regulate a nucleic acid of interest can also be removed or replaced to alter the regulation of the nucleic acid.

Therefore, the invention provides a method of treating a pathological condition in an individual by genetic modification. The method involves contacting a cell of the individual with an effective amount of a targeting construct that includes a cis acting nucleic acid element and targeting sequences. The targeting sequences correspond to a sequence of a nucleic acid involved in the pathological condition. The targeting construct is taken up by the cell and the cis acting nucleic acid element is inserted by homologous recombination into the nucleic acid involved in the pathological condition so as to alter its genetic activity.

Methods of inserting, removing and replacing nucleic acid sequences at predetermined locations using homologous recombination are known in the art and are described, for example, in Yanez et al., Gene Therapy 5:149–159 (1998), which is incorporated herein by reference. A targeting construct is prepared that carries a segment of nucleic acid homologous to the target nucleic acid as well as the desired modified sequences. As described above, the modified sequences can be, for example, a normal or altered copy of a cis acting nucleic acid element that is to be introduced into the target locus. Targeting constructs can be delivered to the target cells by a variety of methods known in the art, including, for example, electroporation, microinjection, optoporation, polybrene, DMSO, DEAEdextran, liposome formulations, gene gun, polyamidoamine dendrimers, synthetic peptides and combinations of these agents and methods, such that they are taken up by the target cells and incorporated into the target nucleic acid. Large targeting constructs for homologous recombination can be incorporated, for example, into plasmids, cosmids or viral vectors, such as retroviral or adenoviral vectors. Alternatively, chimeric DNA-RNA oligonucleotides or small denatured DNA fragments, which include the cis acting nucleic acid element flanked by short targeting sequences, can also be used to introduce a cis acting nucleic acid element into a cell at a predetermined location in the genome.

Homologous recombination can be practiced either ex vivo or in vivo, as needed, depending on the therapeutic strategy. For example, cells of a variety of lineages can be obtained from an individual, genetically modified ex vivo by insertion, deletion or replacement of one or more cis acting nucleic acid elements in order to enhance expression of a beneficial gene or gene product or reduce expression of a harmful gene or gene product, and returned to the same or an immunologically matched individual for therapeutic benefit. Similarly, a targeting construct can be used to directly contact a diseased cell within an individual, so as to be taken up by the cell and inserted into the target nucleic acid that is involved in the pathological condition so as to alter its genetic activity.

Cis acting nucleic acid elements can also be used to identify new genes that may be of importance in diagnosing and treating disease. As known in the art and described above, most structural and regulatory genes are characterized by the presence of cis acting nucleic acid sequences either within or adjacent to the gene. Therefore the presence of a cis acting nucleic acid element is indicative of a nearby gene. For example, cis acting DNA elements can be detectably labeled and used to hybridize to genomic libraries, or libraries of subgenomic regions, using known methods. The genes so identified can be sequenced and identified. This procedure advantageously allows the simultaneous identification of a plurality of genes that are modulated by the same cis acting nucleic acid element or combination of elements.

The invention also provides a method of determining the binding state of a nucleic acid. The method involves contacting a nucleic acid with a plurality of isolated cis acting nucleic acid elements under conditions that allow nucleic acid binding factors bound to the nucleic acid to bind to the isolated cis acting nucleic acid elements. The isolated cis acting nucleic acid elements that bind to the nucleic acid binding factors are identified, and characterize the binding state of the nucleic acid.

Cellular nucleic acid binding factors can either be constitutively bound to cis acting nucleic acid elements or bind in response to appropriate extracellular signals. For example, nucleic acid binding factors can bind cis acting nucleic acid elements as a response to hormones, growth and differentiation factors, stress, pathological conditions, contact with neighboring cells and other such stimuli. Therefore, the binding state of a nucleic acid reflects its response to its environment at the time of detection.

Depending on the desired application of the method, a binding state can be determined for any nucleic acid molecule in a single cell, group of cells or tissue of interest. The nucleic acid is obtained under conditions where it remains bound to its normal nucleic acid binding factors. For example, a chromatin preparation, hnRNA preparation, mRNA preparation, or any fraction of these or other preparations described above, can be obtained from a single cell, group of cells or tissue. By methods described above the nucleic acid preparation is contacted with a plurality of isolated cis acting nucleic acid elements under conditions such that the nucleic acid binding factors will bind to the isolated cis acting nucleic acid elements. As described above, such conditions can, if desired, involve an excess of isolated cis acting nucleic acid elements to shift the equilibrium to favor binding to the isolated cis acting nucleic acid elements.

A plurality of isolated cis acting nucleic acid elements useful in determining the binding state of a nucleic acid can include any type and combination of isolated cis acting nucleic acid elements, as described above, such as cis acting nucleic acid elements that regulate a particular group of genes or are found in a particular cell type of interest. The isolated cis acting nucleic acid elements that bind to nucleic acid binding factors can be distinguished from unbound nucleic acids by any of the methods described above including, for example, retention on nitrocellulose, protection from restriction digestion, and density or size fractionation.

Methods of determining which isolated cis acting nucleic acid elements are bound by a nucleic acid binding factor can also be automated. Automated detection is particularly advantageous in rapidly and reproducibly screening a large number of samples to determine their binding state. For example, oligonucleotides representing known cis acting nucleic acid elements can be synthesized at known positions on arrays. Those cis acting nucleic acid elements that are bound by nucleic acid binding factors have altered properties, in comparison with unbound cis acting nucleic acid elements, as described previously, which allow them to be detected by automated methods known in the art. The type, number, pattern or extent of bound cis acting nucleic acid elements is indicative of the binding state of the nucleic acid being assayed.

A method of the invention can be used to diagnose disease in an individual by comparing the binding state of nucleic acids obtained from a cell, group of cells or tissue of an individual suspected of having a disease with the binding state of nucleic acids obtained from similar cells from a normal individual. As a non-limiting example, the binding state of one or more nucleic acids can be used to diagnose cancer. Cancer is characterized by the enhanced expression of genes that promote the proliferation and metastasis of abnormal cells, such as growth factors, proteases, angiogenic factors, and the like. A method of the invention can be used, therefore, to determine whether cis acting nucleic acid elements that regulate the expression of such genes are bound to nucleic acid binding factors in a particular tissue. Cancer is also characterized by an increase in DNA synthesis. Therefore, a method of the invention can be used to determine whether cis acting nucleic acid elements that regulate DNA synthesis are bound in a particular tissue.

The binding state of nucleic acids can be determined, for example, before and after the administration of a therapeutic agent to monitor the consequences of therapy. For example, if a therapy is successful, the binding state of nucleic acids will more closely resembles the known normal binding state than the previous diseased state.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A method of identifying a nucleic acid containing a cis acting nucleic acid element, comprising:
   (a) contacting a preparation of nucleic acids bound to a diverse population of nucleic acid binding factors with a diverse population of isolated nucleic acid molecules under conditions wherein said nucleic acid binding factors selectively bind said isolated nucleic acid molecules; and
   (b) identifying one or more of the isolated nucleic acid molecules that bind to one or more of the nucleic acid binding factors, wherein an isolated nucleic acid molecule that binds to an nucleic acid binding factor is characterized as a nucleic acid containing a cis acting nucleic acid element.

2. The method of claim 1, wherein said diverse population of isolated nucleic acid molecules comprises 10 or more different nucleic acid molecules.

3. The method of claim 1, wherein said diverse population of isolated nucleic acid molecules comprises greater than about $10^5$ different nucleic acid molecules.

4. The method of claim 1, wherein said diverse population of isolated nucleic acid molecules comprises nucleic acids attached to a solid support.

5. The method of claim 1, wherein said diverse population of nucleic acid binding factors comprises 10 or more different nucleic acid binding factors.

6. The method of claim 1, wherein said diverse population of nucleic acid binding factors comprises greater than about $10^3$ different nucleic acid binding factors.

7. The method of claim 1, wherein said preparation of nucleic acids bound to a diverse population of nucleic acid binding factors is selected from the group consisting of chromatin, a chromosome, a chromosome arm, a transcriptional domain, a gene family and a gene.

8. The method of claim 1, wherein said diverse population of isolated nucleic acid molecules comprises greater than about 200 different nucleic acid molecules.

9. The method of claim 1, wherein said diverse population of isolated nucleic acid molecules comprises greater than about $10^3$ different nucleic acid molecules.

10. The method of claim 1, wherein said diverse population of isolated nucleic acid molecules comprises greater than about $10^8$ different nucleic acid molecules.

11. The method of claim 1, wherein said diverse population of nucleic acid binding factors comprises greater than about 100 different nucleic acid binding factors.

* * * * *